United States Patent [19]

Stürm et al.

[11] 4,339,446
[45] Jul. 13, 1982

[54] 5-SULFAMOYL-ORTHANILIC ACIDS, PROCESSES FOR THEIR PREPARATION AND THEIR USE AS MEDICAMENTS

[75] Inventors: Karl Stürm, Heidesheim; Roman Muschaweck, Frankfurt am Main, both of Fed. Rep. of Germany

[73] Assignee: Hoechst Aktiengesellschaft, Frankfurt am Main, Fed. Rep. of Germany

[21] Appl. No.: 236,605

[22] Filed: Feb. 20, 1981

[30] Foreign Application Priority Data

Feb. 22, 1980 [DE] Fed. Rep. of Germany ....... 3006686

[51] Int. Cl.³ .................... A61K 31/63; C07C 143/80; C07D 307/36
[52] U.S. Cl. ............................ 424/228; 260/397.7 R; 260/456 A; 424/229; 549/75; 549/492
[58] Field of Search ..................... 260/397.7 R, 347.2; 549/75; 424/228, 229

[56] References Cited

U.S. PATENT DOCUMENTS

| | | | |
|---|---|---|---|
| 3,812,104 | 5/1974 | Werner | 260/397.7 R |
| 3,860,582 | 1/1975 | Schoenberg et al. | 260/397.7 R |
| 3,875,150 | 4/1975 | Feit et al. | 260/397.7 R |
| 3,914,219 | 10/1975 | Lerch et al. | 260/397.7 R |

FOREIGN PATENT DOCUMENTS

| | | |
|---|---|---|
| 315827 | 6/1974 | Austria. |
| 2142758 | 3/1973 | Fed. Rep. of Germany. |
| 2232457 | 1/1974 | Fed. Rep. of Germany. |

OTHER PUBLICATIONS

Physicians Desk Reference, 35th edition, pp. 938–939 (1981).
Merck Index, 9th edition, p. 555 (1976).
Sturm et al., Chem. Abstract, 90, 87034n (1979), (Abstract of Ger. Offen. No. 2,718,871).

*Primary Examiner*—Nicky Chan
*Attorney, Agent, or Firm*—Curtis, Morris & Safford

[57] ABSTRACT

What are disclosed are compounds of the formula

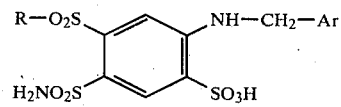

in which R denotes alkyl, alkenyl, cycloalkyl or cycloalkylalkyl, each of which has up to 10 C atoms, or phenyl and Ar denotes phenyl, thienyl or furyl and salts thereof, the preparation of these compounds and their use as medicaments and also medicaments of this type as such.

6 Claims, No Drawings

5-SULFAMOYL-ORTHANILIC ACIDS, PROCESSES FOR THEIR PREPARATION AND THEIR USE AS MEDICAMENTS

The invention relates to compounds of the formula I, which can be allocated to the group of 5-sulfamoyl-orthanilic acids, and physiologically acceptable salts thereof.

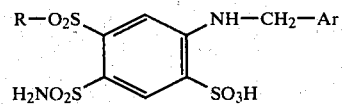

In the formula, R denotes alkyl, alkenyl, cycloalkyl or cycloalkyalkyl, each of which has up to 10 C atoms, or phenyl and Ar denotes phenyl, thienyl or furyl.

If R represents alkyl or alkenyl, this can be straight-chain or branched. Preferred alkyls or alkylenes are those having 4 to 6 C atoms. If R represents a cyclic radical, rings having 5 to 8 members are preferred. Accordingly, R can be represented, in particular, by cyclopentyl, cyclohexyl, cycloheptyl, cyclohexylmethyl, n-butyl, isobutyl, n-pentyl or n-hexyl. 2-Furyl and 2-thienyl are of primary interest as Ar.

All physiologically acceptable cations, particularly alkali metal or alkaline earth metal ions, ammonium or substituted ammonium are suitable for forming salts.

The invention relates further to a process for the preparation of the compounds of the formula I. The process comprises (a) saponifying under alkaline conditions an ester of the formula II

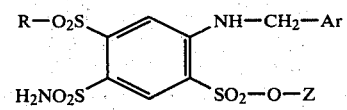

in which Z denotes aryl;

(b) reacting a compound of the formula III

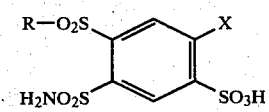

in which X denotes halogen, or a salt thereof, with an amine of the formula

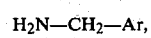

or (c) oxidizing a compound of the formula V

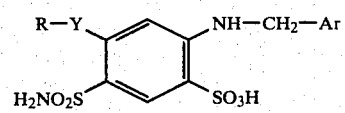

in which Y denotes —S— or —SO—, or a salt thereof, to give the sulfone, and optionally converting the resulting compound into the free acid or a salt.

In procedure (a) any aromatic radical is suitable, in principle, as the radical Z in the starting material of the formula II; for industrial synthesis, however, it is particularly advantageous to use the phenyl or cresyl esters, which are easy to prepare.

The alkaline saponification of the esters is preferably carried out in an aqueous medium using an inorganic base, in particular using excess 1N to 5N sodium hydroxide or potassium hydroxide solution.

For example, the phenyl or cresyl esters can be completely saponified on a steam bath in the course of one hour by means of 2N aqueous sodium hydroxide or potassium hydroxide solution. The end products crystallize out immediately from the clear saponification solution in the form of their sodium or potassium salts, respectively, if the solution is neutralized at room temperature with a mineral acid, preferably hydrochloric acid, or an organic acid, such as acetic acid. The potassium salts are generally more sparingly soluble in water than the corresponding sodium salts. The phenol liberated in the saponification is in some cases precipitated together with the process product, particularly if a cresyl, xylyl, nitrophenyl, chlorophenyl or naphthyl ester has been used as the starting material instead of the phenyl ester.

The residue of these phenols can then be removed by washing the precipitate thoroughly with an organic solvent. Solvents in which the products are virtually insoluble, such as ethanol, isopropanol, diethyl ether, diisopropyl ether, acetone or tetrahydrofuran, are used for this purpose. Final traces of phenol which may still be present can be removed by subsequently recrystallizing the products from aqueous alcohols.

The starting materials of the formula II can be prepared, for example, from the 2,4-dichloro-5-sulfamoyl-benzenesulfonic acid aryl esters of the formula VI, which are described in German Auslegeschrift No. 2,718,871, in accordance with the following reaction:

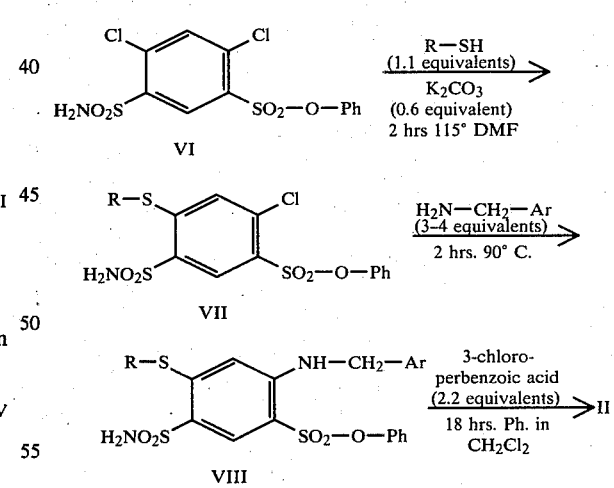

In procedure (b) it is preferable to employ the alkali metal salts of compounds in which X denotes fluorine or chlorine, as the starting materials of the formula III. The reaction with the amine of the formula IV is advantageously effected at a temperature between 80° and 100° C., if X denotes fluorine, and is advantageously effected at a temperature between 120° and 140° C., if X denotes chlorine. An acid-binder, for example sodium carbonate, potassium carbonate or a tertiary amine, can be added to the reaction batch in order to bind the hydrogen halide formed. It is particularly advantageous to use the base IV itself as the acid binder by employing it in a 2-molar to 3-molar excess.

The solvents used in this reaction are, in particular, strongly polar, water-miscible organic solvents, such as dimethylsulfoxide or dimethylformamide.

After the completion of the reaction, the solvent and excess amine are removed, advantageously by being distilled off completely. The residue is treated with water and the crude end product is purified as described for procedure (a).

The starting materials of formula III can be obtained in a simple manner by oxidizing the compounds VII (with $H_2O_2$ or an organic per-acid), followed by alkaline saponification.

In procedure (c), a thioether or a sulfoxide of the formula V is oxidized to give the corresponding sulfone. If Ar denotes phenyl or thienyl, it is advantageous to carry out this oxidation with perhydrol in glacial acetic acid or with peracetic acid/glacial acetic acid at a temperature between 20° and 60° C. Compounds of the formula V in which Ar denotes furyl are advantageously oxidized in a dilute solution at room temperature using the calculated quantity of per-acid. An example of a suitable solvent for this reaction is a mixture of methylene chloride and dimethylformamide and an example of a suitable oxidizing agent is 3-chloroperbenzoic acid. It is advantageous to isolate the end products by recrystallization from aqueous 1N $KHCO_3$ or 1N $NaHCO_3$ solution, after removing the solvent.

The starting materials of the formula V can be obtained in a simple manner from sulfonic acid aryl esters of the formula VIII by saponification or by oxidation to give the sulfoxide with subsequent saponification.

In the form of their alkali metal, alkaline earth metal or ammonium salts, the compounds according to the invention are stable, colorless substances which crystallize readily. They are not particularly readily soluble in water at room temperature. They can, therefore, be recrystallized extremely well from water or water containing organic solvents, such as alcohols, acetone, dioxane, tetrahydrofuran or dimethylformamide. Amongst the metal salts, the sodium salts are the most water soluble. They can, therefore, be converted particularly easily into other metal salts by double decomposition in aqueous solution with appropriate water-soluble salts.

The salts with hydroxyamines, for example with mono-, di- or tri-ethanolamine or with glucosamine, are even more soluble in water than the sodium salts.

The compounds can also be isolated in the form of free sulfonic acids. This can be done, for example, by treating the sodium salts with 5N HCl. The free acids are not very stable, however, particularly if Ar represents furyl.

For therapeutical purposes, therefore, the free acids are less suitable. The sodium and potassium salts, on the other hand, are particularly suitable for formulations of medicaments. The salts with basic, potassium-retaining compounds, such as amiloride or triamterene or the salts with basic anti-hypertensive agents, such as clonidine, dihydralazine or guanethidine or with β-blockers, such as propranolol, timolol, penbutolol or pindolol, are also of great pharmacological importance.

The compounds according to the invention are salidiuretics of the furosemide type and have an exceptionally high potency. Compared with known compounds of this type, they are also distinguished by having a particularly low elimination of potassium and a pronounced uricosuric effective component.

Oral administration of the products, particularly in the form of tablets, dragées or capsules containing 0.1 to 50 mg of active compound is particularly suitable for human therapy, and, in addition, also intravenous administration using aqueous injection solutions containing 0.1 to 10 mg of active compound.

EXAMPLE 1

Sodium N-(2-furylmethyl)-4-cyclohexylsulfonyl-5-sulfamoyl-orthanilate 55.5 g (0.1 mole) of N-(2-furylmethyl)-4-cyclohexylsulfonyl-5-sulfamoyl-orthanilic acid phenyl ester, having a melting point of 133° C. (recrystallized from methanol), are stirred with 0.4 l of 2N NaOH for 1 hour at 95° C. The clear reaction solution is then cooled to room temperature and the pH is adjusted to 7 with 5N HCl. After standing for one hour at room temperature, the end product, which has separated out in a crystalline form, is filtered off, washed successively with ice water and absolute ethanol and dried at 90° C.

Yield: 44 g (88% of theory), decomposition point 300° C.

EXAMPLE 2

Potassium N-(2-furylmethyl)-4-cyclohexylsulfonyl-5-sulfamoyl-orthanilate 42 g of 90 percent strength 3-chloroperbenzoic acid (0.22 mole) are added in portions and while stirring, at room temperature, to a solution in 1.0 l of dimethylformamide of 48.5 g (0.1 mole) of potassium N-(2-furylmethyl)-4-cyclohexylmercapto-5-sulfamoyl-orthanilate, having a decomposition point of 227° C. (recrystallized from water). After standing overnight at room temperature, the dimethylformamide is stripped off in vacuo, 1.0 l of water is added to the residue and the pH is adjusted to 8 with 2N KOH. After standing for one hour at 15°, the end product, which has separated out in a crystalline form, is filtered off and purified by recrystallization from water, with the addition of active charcoal.

Yield: 41 g (79% of theory), decomposition point 305° C.

EXAMPLE 3

Sodium N-(2-thienylmethyl)-4-cyclohexylsulfonyl-5-sulfamoyl-orthanilate 57.1 g (0.1 mole) of N-(2-thienylmethyl)-4-cyclohexylsulfonyl-5-sulfamoyl-orthanilic acid phenyl ester, having a melting point of 193° C., are saponified analogously to Example 1 with 2N NaOH and the end product is isolated as described in that example.

Yield: 48.5 g (84% of theory), decomposition point 310° C.

EXAMPLE 4

Sodium N-benzyl-4-cyclohexylsulfonyl-5-sulfamoyl-orthanilate 56.4 g (0.1 mole) of N-benzyl-4-cyclohexylsulfonyl-5-sulfamoyl-orthanilic acid phenyl ester are saponified analogously to Example 1 with 0.4 l of 2N NaOH and the end product is recrystallized from 30 percent strength ethanol.

Yield: 43 g (84% of theory), decomposition point 296° C.

EXAMPLE 5

Potassium N-(2-furylmethyl)-4-phenylsulfonyl-5-sulfamoyl-orthanilate 45.0 g (0.1 mole) of potassium 2-chloro-4-phenylsulfonyl-5-sulfamoylbenzenesulfonate are stirred with a mixture of 0.1 l of furfurylamine and 0.1 l of dimethyl sulfoxide for 2 hours at 125°–130° C. Excess furfurylamine and dimethyl sulfoxide are then distilled off in vacuo, 0.1 l of water is added to the residue and the pH of the mixture is adjusted to 7 with 5N HCl. After standing at room temperature for one hour, the end product, which has precipitated in a crystalline form, is filtered off and purified by recrystallization from water.

Yield: 35 g (70% of theory), decomposition point 270° C.

EXAMPLE 6

Sodium N-(2-furylmethyl)-4-cycloheptylsulfonyl-5-sulfamoyl-orthanilate 56.9 g (0.1 mole) of N-(2-furylmethyl)-4-cycloheptylsulfonyl-5-sulfamoyl-orthanilic acid phenyl ester, having a melting point of 163° C. (recrystallized from methanol), are saponified analogously to Example 1 with sodium hydroxide solution and the end product is isolated as described in that example.

Yield: 44 g (86% of theory), decomposition point 284° C.

EXAMPLE 7

Potassium N-(2-furylmethyl)-4-n-butylsulfonyl-5-sulfamoyl-orthanilate 45.8 g (0.1 mole) of potassium N-(2-furylmethyl)-4-n-butylmercapto-5-sulfamoyl-orthanilate, having a decomposition point of 245° C. (recrystallized from water), are dissolved in 0.1 l of dimethyl sulfoxide, the solution is diluted with 0.3 l of methylene chloride, 48 g (0.25 mole) of 90 percent strength 3-chloroperbenzoic acid are added at room temperature, while stirring, and the mixture is left to stand overnight at room temperature. The solvent is then stripped off in vacuo, the residue is digested with 0.3 l of warm 1N KHCO₃ solution in order to remove the 3-chlorobenzoic acid and the end product, which remains undissolved, is purified by subsequent recrystallization from water.

Yield: 24 g (49% of theory), decomposition point 330° C.

EXAMPLE 8

0.1 mole of N-(2-furylmethyl)-4-n-propylsulfonyl-5-sulfamoyl-orthanilic acid phenyl ester, having a melting point of 145° C. (recrystallized from methanol), is saponified analogously to Example 1 with NaOH and the end product is isolated as described in that example.

Yield: 35 g (76% of theory), decomposition point 320° C.

EXAMPLE 9

Sodium N-(2-furylmethyl)-4-cyclopentylsulfonyl-5-sulfamoyl-orthanilate 54.1 g (0.1 mole) of N-(2-furylmethyl)-4-cyclopentylsulfonyl-5-sulfamoyl-orthanilic acid phenyl ester, having a melting point of 169° C. (recrystallized from a 1:2 mixture of methanol and dimethylformamide), are saponified analogously to Example 1 with NaOH. The end product, which is precipitated at pH 7 with HCl, is washed on the filter with water and then with ethanol and is dried at 90° C.

Yield: 40 g (82% of theory), decomposition point 285° C.

EXAMPLE 10

Potassium N-(2-furylmethyl)-4-allylsulfonyl-5-sulfamoyl-orthanilate 51.3 g (0.1 mole) of N-(2-furylmethyl)-4-allylmercapto-5-sulfamoyl-orthanilic acid phenyl ester, having a melting point of 138° C. are warmed with 0.4 l of 2N KOH for half an hour on a steam bath, while stirring. After the reaction solution has been cooled to room temperature and neutralized with 5N HCl, the mixture is evaporated to dryness, the residue is extracted with 0.1 l of hot dimethylformamide and the end product is precipitated in a crystalline form from the filtered solution by adding 0.4 l of diisopropyl ether.

Yield: 35 g (74% of theory), decomposition point 125° C.

EXAMPLE 11

Sodium N-(2-furylmethyl)-4-cyclohexylmethylsulfonyl-5-sulfamoyl-orthanilate 56.7 g (0.1 mole) of N-(2-furylmethyl)-4-cyclohexylmethylsulfonyl-5-sulfamoyl-orthanilic acid phenyl ester, having a melting point of 152° C. (from ethanol) are warmed with 0.4 l of 2N NaOH for 45 minutes on a steam bath, while stirring, and the end product is isolated analogously to Example 1.

Yield: 46 g (90% of theory), decomposition point 350° C.

EXAMPLE 12

Potassium N-(2-furylmethyl)-4-methylsulfonyl-5-sulfamoyl-orthanilate 48.6 g (0.1 mole) of N-(2-furylmethyl)-4-methylsulphonyl-5-sulfamoyl-orthanilic acid phenyl ester, having a melting point of 175° C. (from methanol), are saponified by warming for one hour on a steam bath with 0.4 l of 2N KOH and the end product is isolated analogously to Example 1.

Yield: 36.5 g (81% of theory), decomposition point 225° C.

EXAMPLE 13

Sodium N-(2-thienylmethyl)-4-cyclopentylsulfonyl-5-sulfamoyl-orthanilate 55.7 g (0.1 mole) of N-(2-thienylmethyl)-4-cyclopentylsulfonyl-5-sulfamoyl-orthanilic acid phenyl ester, having a melting point of 194° C. (from methanol), are saponified by heating for one hour on a steam bath with 0.4 l of 2N NaOH and the end product is isolated analogously to Example 1.

Yield: 42.5 g (85% of theory), decomposition point 278° C.

EXAMPLE 14

Sodium N-(2-furylmethyl)-4-n-hexylsulfonyl-5-sulfamoyl-orthanilate 48.7 g (0.1 mole) of N-(2-furylmethyl)-4-n-hexylsulfonyl-5-sulfamoyl-orthanilic acid phenyl ester, having a melting point of 140° C. (from methanol), are heated with 0.4 l of 2N NaOH for 45 minutes under reflux. The pH of the clear reaction solution is then adjusted at room temperature to 7 with 5N HCl and the end product, which has precipitated in a crystalline form, is filtered off after one hour, washed with absolute ethanol and dried at 90° C.

Yield: 43 g (85% of theory), decomposition point 209° C.

In addition to the compounds described above, the following process products can also be obtained in an analogous manner: potassium N-(2-furylmethyl)-4-ethylsulfonyl-5-sulfamoyl-orthanilate, sodium N-(2-thienylmethyl)-4-ethylsulfonyl-5-sulfamoyl-orthanilate, sodium N-(2-furylmethyl)-4-isopropylsulfonyl-5-sulfamoyl-orthanilate, sodium N-(2-thienylmethyl)-4-n-propylsulfonyl-5-sulfamoyl-orthanilate, potassium N-(2-thienylmethyl-4-n-butylsulfonyl-5-sulfamoyl-orthanilate, sodium N-benzyl-4-n-butylsulfonyl-5-sulfamoyl-orthanilate, potassium N-(2-furylmethyl)-4-isobutylsulfonyl-5-sulfamoyl-orthanilate, potassium N-(2-thienylmethyl)-4-isobutylsulfonyl-5-sulfamoyl-orthanilate, sodium N-(2-thienylmethyl)-4-allylsulfonyl-5-sulfamoyl-orthanilate, potassium N-(2-furylmethyl)-4-n-pentylsulfonyl-5-sulfamoyl-orthanilate, potassium N-(2-furylmethyl)-4-n-octylsulfonyl-5-sulfamoyl-orthanilate, potassium N-(2-furylmethyl)-4-cyclopropylsulfonyl-5-sulfamoyl-orthanilate, sodium N-(2-furylmethyl)-4-cyclopropylmethylsulfonyl-orthanilate, sodium N-(2-furylmethyl)-4-cyclobutylmethylsulfonyl-5-sulfamoyl-orthanilate, potassium N-(2-furylmethyl)-4-cyclopentylmethylsulfonyl-5-sulfamoyl-orthanilate, sodium N-(3-furylmethyl)-4-cyclohexylsulfonyl-5-sulfamoyl-orthanilate, sodium N-(2-thienylmethyl)-4-cycloheptylsulfonyl-5-sulfamoyl-orthanilate, potassium N-(2-furylmethyl)-4-cyclooctylsulfonyl-5-sulfamoyl-orthanilate and sodium N-(2-furylmethyl)-4-cyclooctylmethylsulfonyl-5-sulfamoyl-orthanilate.

We claim:

1. A compound of the formula

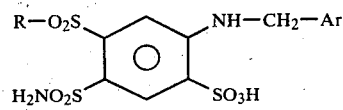

or a physiologically acceptable salt thereof wherein R is alkyl, alkenyl, cycloalkyl, or cycloalkylalkyl, each having up to 10 carbon atoms, or R is phenyl, and Ar is phenyl, thienyl, or furyl.

2. A compound or salt as in claim 1 wherein R is cyclopentyl, cyclohexyl, cycloheptyl, cyclohexylmethyl, n-butyl, isobutyl, n-pentyl, or n-hexyl, and R is 2-furyl or 2-thienyl.

3. A compound or salt as in claim 1 wherein R is n-butyl and Ar is 2-furyl.

4. A compound as in claim 1 wherein R is cyclohexyl and Ar is 2-furyl.

5. A salidiuretic pharmaceutical preparation comprising a salidiuretically effective amount of a compound or salt as in claim 1 together with a pharmaceutically acceptable carrier for the oral or intravenous administration thereof.

6. A method for inducing salidiuresis in a patient in need of such treatment, which method comprises orally or intravenously administering to said patient a salidiuretically-effective amount of a compound or salt as in claim 1.

* * * * *